United States Patent [19]

Matsuda et al.

[11] Patent Number: 5,457,141
[45] Date of Patent: Oct. 10, 1995

[54] SURGICAL ADHESIVE SHEET, SURGICAL INSTRUMENTS AND METHODS OF USING THE SAME

[75] Inventors: Takehisa Matsuda, Minoo; Tetsuo Itoh, Shiga; Tohru Tani, Kusatsu, all of Japan

[73] Assignee: Sanyo Chemical Industries, Ltd., Kyoto, Japan

[21] Appl. No.: 127,477

[22] Filed: Sep. 28, 1993

Related U.S. Application Data

[63] Continuation of Ser. No. 497,985, Mar. 23, 1990, abandoned.

[30] Foreign Application Priority Data

| Mar. 23, 1989 | [JP] | Japan | 1-71407 |
| Mar. 23, 1989 | [JP] | Japan | 1-71408 |
| Mar. 23, 1989 | [JP] | Japan | 1-71409 |

[51] Int. Cl.⁶ ............................. A61F 13/02; C08G 18/06
[52] U.S. Cl. ...................... 523/111; 523/118; 428/423.3; 428/423.5; 428/424.6; 428/425.1; 428/425.5; 428/424.4; 428/424.8; 424/448; 602/52; 602/54; 528/905
[58] Field of Search ..................... 523/111, 118; 428/423.3, 423.5, 424.6, 425.1, 425.5, 424.4, 424.8; 528/905; 524/448; 602/52

[56] References Cited

U.S. PATENT DOCUMENTS

| 3,284,274 | 11/1966 | Hulslander et al. | 428/423.3 |
| 4,057,535 | 11/1977 | Lipatova et al. | 424/78.37 |
| 4,140,125 | 2/1979 | Smith | 606/158 |
| 4,376,438 | 3/1983 | Straube et al. | 523/111 |
| 4,412,054 | 10/1983 | Yamabe et al. | 528/70 |
| 4,427,003 | 1/1984 | Fennimore et al. | 523/111 |
| 4,433,680 | 2/1984 | Yoon | 523/111 |
| 4,477,604 | 10/1984 | Oechscle, III | 523/116 |
| 4,621,029 | 11/1986 | Kawaguchi | 428/447 |
| 4,740,534 | 4/1988 | Matsuda et al. | 523/111 |
| 4,743,632 | 5/1988 | Marinovic | 524/60 |
| 4,804,691 | 2/1989 | English et al. | 528/54 |
| 4,806,614 | 2/1989 | Matsuda et al. | 528/59 |
| 4,829,099 | 5/1989 | Fuller et al. | 528/58 |
| 4,994,542 | 2/1991 | Matusda et al. | 528/70 |
| 5,169,720 | 12/1992 | Braatz et al. | 428/424.6 |
| 5,173,301 | 12/1992 | Itoh et al. | 523/118 |

FOREIGN PATENT DOCUMENTS

| 0332405 | 9/1989 | European Pat. Off. |
| 2237610 | 2/1975 | France |
| 2597743 | 10/1987 | France |
| 89/2101 | 1/1989 | Japan |
| 84/03035 | 8/1984 | WIPO |

OTHER PUBLICATIONS

Redo et al., "Arch Surg", vol. 93, pp. 319–322, Aug. 1966.
Healey et al., "Annals of Surgery", Jun. 1962, pp. 817–826.
Healey et al., "Surgery" vol. 51, No. 4, Apr. 1962, pp. 452–455.
Braunwald et al., "Surgery", vol. 51, No. 6, Jun. 1962, pp. 786–792.
J. Biomed. Mater. Res., vol. 8, No. 1, pp. 35–43, Jan., 1974, E. Llewellyn–Thomas, et al., "Adhesion of Synthetic Organic Polymer on Soft Tissue. I. A Fast Setting Polyurethane Adhesive".

Primary Examiner—Paul R. Michl
Assistant Examiner—Andrew E. C. Merriam
Attorney, Agent, or Firm—Oblon, Spivak, McClelland, Maier & Neustadt

[57] ABSTRACT

A sheet material, coated with a surgical adhesive comprising an NCO-terminated urethane prepolymer, is used for bonding of tissues, with improved handleability.

Surgical instruments, comprising a non-adherent material towards an NCO-terminated urethane prepolymer, are used for application of surgical adhesive. Such instruments, comprising a rod tapered so that the tip can be partly inserted into blood vessel, are suitable for anastomosis of blood vessel.

3 Claims, 5 Drawing Sheets

SURGICAL ADHESIVE SHEET, SURGICAL INSTRUMENTS AND METHODS OF USING THE SAME

This is a continuation of application Ser. No. 07/497,985, Mar. 23, 1990, now abandoned.

BACKGROUND OF THE INVENTION

1. Field of the Invention:

This invention relates to application of surgical adhesive. More particularly, it relates to application means, instruments and methods, for surgical adhesive comprising an NCO-terminated prepolymer.

2. Description of the Prior Art:

As surgical adhesives, there have been known heretofore those comprising a hydrophilic urethane prepolymer prepared by reaction of organic polyisocyanate with polyether polyol (for example, JPN Patent Lay-open No. 148866/1987=U.S. Pat. Nos. 4,740,534 and 4,806,614).

Such adhesives comprising prepolymer, however, have drawbacks that, due to their high viscosity and high adhesive power, they are of poor handleability, that it is difficult to apply only a necessary amount to a fixed place to be bound, and use of adhesives in an amount more than needed causes adhesion with other part of living tissue and gets into trouble other than treatment purpose, and that they must be used quickly because such prepolymer is rapidly cured by reaction with water or body fluid on tissue surface.

In bonding of arterioles with surgical adhesives, vessel is bonded in collapsed state to result in obliteration of vessel.

SUMMARY OF THE INVENTION

It is an object of the present invention to provide application means of surgical adhesive comprising NCO-terminated urethane prepolymer, with improved handleability.

It is another object of this invention to provide a surgical adhesive manufactured in the form easily handled for bonding tissue.

It is still another object of the invention to provide a surgical instrument, suitable for application of surgical adhesive.

It is yet another object of the invention to provide a surgical instrument suitable for anastomosis of blood vessel.

Briefly, these and other objects of the present invention as hereinafter will become more readily apparent have been attained broadly by a surgical adhesive sheet, which comprises a sheet material coated with a surgical adhesive comprising an NCO-terminated urethane prepolymer; a surgical instrument for application of a surgical adhesive, comprising a non-adherent material towards an NCO-terminated urethane prepolymer; and a instrument for anastomosis of blood vessel, which comprises a rod tapered so that the tip can be partly inserted into blood vessel.

DETAILED DESCRIPTION OF THE PREFERRED EMBODIMENTS

Suitable sheet materials, for use in producing said surgical adhesive sheet of the present invention, include non-biodegradable ones and biodegradable ones.

Illustrative examples of non-biodegradable sheet materials are those of polymers, including those obtainable by addition polymerization, for instance, olefinic polymers (such as polyethylenes, ethylene copolymers, polypropylenes, polybutenes and the like), acrylic and methacrylic resins (such as polymers and copolymers of acrylate, methacrylate or/and acrylonitrile), hydroxyl-containing polymers (such as polyvinyl alcohols), halogen-containing polymers (such as vinyl chloride resins, polyvinylidene chlorides, fluorine-containing resins, rubber hydrochlorides and chloroprene polymers), diene polymers (such as butadiene polymers and isoprene polymers), and the like; and polycondensation polymers, for example, polyesters, polycarbonates, polyamides, polyimides, polyurethane resins, silicone resins, and the like. Among these, preferred are polyurethane resins, silicone resins and fluorine-containing resins.

Biodegradable sheet materials include, for example, those of natural and synthetic polymers written in WO 84/03035 (JPN Tokuhyo Sho60-500485). Exemplary of biodegradable natural polymers are partially oxidized celluloses, chitin and derivatives thereof, collagen and derivatives thereof, and the like. Suitable biodegradable synthetic polymers are inclusive of polyamino acids, polyamino acid copolymers and derivatives thereof, polylactic acids, polyglycolic acids, copolymers of lactic acid and glycolic acid, polymers of hydroxybutyric acid, and so on. Among these, preferred are polyamino acids, polyamino acid copolymers and derivatives thereof, polyglycolic acids, copolymers of lactic acid and glycolic acid.

Two or more of these polymers may also be used.

Sheet materials in this invention can be in various forms, for instance, continuous films; films having a plurality of openings therein; and porous sheets, such as non-woven and woven fabrics, and the like.

Sheet materials may be usually 5 microns–10 mm thick, closely depending upon the form. According to the part to be applied, application method and object, there can be taken various combinations of forms and thickness of sheet materials.

In case of films having openings or porous sheets, the surface may be laminated with water vapor-permeable and air-permeable films (such as silicone resin film, polyurethane resin film and the like), having no permeability to micro-organisms (such as bacteria), to prevent infection.

Suitable surgical adhesives usable in the invention include ones comprising NCO-terminated urethane prepolymer.

As such prepolymer for adhesive used in this invention, preferred are NCO-terminated hydrophylic urethane prepolymers, derived from at least one organic polyisocyanate (a) and at least one hydrophilic polyether polyol (b) with or without one or more other polyols (c). Suitable examples of these prepolymers and the raw materials (a), (b) and (c) are those written in U.S. Pat. No. 4,806,614 and EP Patent 382,405.

Suitable polyisocyanates (a) include aromatic polyisocyanates containing 6–20 carbon atoms [such as tolylene diisocyanate (TDI), diphenylmethane diisocyanate (MDI), p-phenylene diisocyanate (PPDI) and the like], aliphatic polyisocyanates containing 2–18 carbon atoms, alicyclic polyisocyanates containing 4–15 carbon atoms, araliphatic polyisocyanates containing 8–15 carbon atoms, except carbon atoms in NCO groups, and modified polyisocyanates of these polyisocyanates containing one or more of urethane, carbodiimide, allophanate, urea, biuret, urethdione, urethimine, isocyanurate and oxazolidone groups, as described in U.S. Pat. No. 4,806,614; and fluorine-containing polyisocyanates, as written in EP Patent 332,405, such as those represented by the general formula: OCN—Rf—NCO or OCN—$CH_2$—Rf—$CH_2$—NCO (wherein Rf represents perfluoroalkylene group containing 1–20 carbon atoms, which may contain one or more ether linkages). Among these polyisocyanates, preferred are fluorine-containing ones.

Suitable hydrophilic polyether polyols (b) include adducts of ethylene oxide [hereinafter referred to as EO] or combinations thereof with one or more other alkylene oxides [hereinafter referred to as AO] to one or more compounds containing at least two active hydrogen atoms, for example, polyhydric alcohols (such as ethylene glycol, propylene glycol, and the like), polyhydric phenols, polyester polyols, amines, polycarboxylic acids, phosphorous acids and the like. Addition of EO or combination of EO with AO [random-addition, block-addition or combination of them (such as random-addition followed by block-addition)] to active hydrogen atom-containing compounds can be carried out in the usual way, with or without catalysts [such as alkaline catalysts, amine catalysts and acidic catalysts], under normal or an elevated pressure, in a single step or multi-stages. Hydrophilic polyether polyols have equivalent weight (molecular weight per hydroxyl group) of usually 100–5,000, preferably 200–3,000, and oxyethylene content of usually at least 30%, preferably 50–90% by weight. Content of the primary hydroxyl groups of polyether polyols is preferably at least 30%, more preferably at least 50%, most preferably at least 70%.

Other polyols (c) include low molecular weight polyols and/or hydrophobic polyols. Examples of such polyols are polyhydric alcohols mentioned above [as raw materials for (b)]; AO adducts (such as propylene oxide adducts) of active hydrogen atom-containing compounds as mentioned above (polyhydric alcohols and others); and polyester polyols [for example, condensation products of dihydric and/or trihydric alcohols (such as ethylene glycol, propylene glycol, 1,3- and 1,4-butane diols, 1, 6-hexane diol, neopentyl glycol, diethylene glycol, glycerol, trimethylolpropane and the like) and/or polyether polyols (such as those described above) with dicarboxylic acids (aliphatic or aromatic dicarboxylic acids, such as glutaric, adipic, sebacic, fumaric, maleic, phthalic and terephthalic acids) or ester-forming derivatives thereof (anhydrides and lower alkyl esters, such as maleic and phthalic anhydrides, dimethyl terephthalate, and the like); ring-opening polymerization products of lactones [such as epsilon-caprolactone]. Among these polyols, polyether polyols are preferred.

These polyols [(b) and optionally (c)], used for producing NCO-terminated urethane prepolymer, have equivalent weight (average) of usually 100–5,000, preferably 200–3,000 and usually 2–8 hydroxyl groups, preferably 2–4 hydroxyl groups.

In reacting at least one polyisocyanate (a) with at least one hydrophylic polyether polyol (b) and optionally one or more other polyols (c) to form NCO-terminated hydrophlic urethane prepolymers, ratio of NCO/OH is usually 1.5–5.0, preferably 1.7–3.0. The reaction of (a) with (b) and optionally (c) forming prepolymers can be performed in the usual manner. The reaction may be carried out in the presence of a catalyst. Prepolymers may be prepared by reacting (a) with a mixture of (b) and (c), or reacting successively in any order with (b) and (c). Prepolymers may be prepared by blending a prepolymer from (b) with a prepolymer from (c) [for instance, blending with a prepolymer from a low molecular weight polyol (equivalent weight 50–500) to reduce viscosity].

Preferable prepolymers are NCO-terminated hydrophylic urethane prepolymers, as described above; but, in stead of or in conjunction with such hydrophilic prepolymer, there may also be used other NCO-terminated urethane prepolymers, such as those derived from at least one organic polyisocyanate (a) with one or more other polyols (c), polyamines and the like. Examples of these the raw materials (a), (c), polyamines and the like include those written in "Handbook of Polyurethane Resins" (published 1987 by Nikkan Kogyo Shinbunsha) and also in U.S. Pat. No. 4,806,614 and EP Patent 332,405. These prepolymers can be produced in the same manner as hydrophilic prepolymers mentioned above, except that (b) is not used.

NCO-contents of NCO-terminated hydrophilic prepolymers are usually 1–10%, preferably 2–8% by weight.

In surgical adhesives used in this invention, urethane prepolymers can be used in combination with other adhesive components, for example, unsaturated cyano compound containing cyano group attached to a carbon atom constituting the polymerizable double bond, such as cyano(meth)acrylic acids and esters thereof, as described in U.S. Pat. No. 4,740,534.

Surgical adhesives used in this invention may contain, if necessary, one or more other components, for example, physiologically active materials or medicinal drugs [such as agents affecting central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobias, local anesthetics, antihistaminics, antiphlogistics, astringents, vitamins, antifungal agents, peripheral nervous anesthetics, vasodilators, crude drug essences, tinctures, crude drug powders, hypotenslve agents, and the like], fillers [for example, carbon black, metal oxides, such as red iron oxide and titanium dioxide, silicates, such as calcium silicates and sodium silicates, acrylic resin powders, various ceramic powders, and the like]; softening agents [such as DBP (dibutylphosphate), DOP (dioctylphosphate), TCP (tricresyl-phosphate), tributoxyethylphosphates, and other esters of various types]; stabilizers, such as trimethyldihydroquinone, phenyl-beta-naphthyl amine, p-isopropoxy-diphenyl-amine, diphenyl-p-phenylene diamine, and the like. These additives may be used in an amounts of usually 0–20%, preferably 0–5, based on the weight of the adhesive. If necessary, one or more organic inert solvents, such as methyl ethyl ketone, acetone, toluene, xylene, ethyl acetate, dimethylformamide and the like, may be added to dilute and reduce viscosity of adhesives.

The amount of surgical adhesive in surgical adhesive sheet of the invention, which may vary in accordance with the part to be applied and application purpose, is usually 10–10,000 $g/m^2$, preferably 100–5,000 $g/m^2$.

Surgical adhesive sheets can be produced by various methods, for instance, by direct coating of adhesive onto sheet, by coating adhesive onto release paper followed by transferring the coating to sheet, by coating adhesive continuously or intermittently, by covering adhesive-coated surface with release paper or the like to obtain adhesive sheet having a backing of release paper or the like, or by other methods known in production of pressure-sensitive adhesives. These methods can be applied to any sheet of non-biodegradable ones and biodegradable ones. Adhesive can be applied to sheet on one side or on both sides, with any known application means, such as by using brushes, tweezers, applicators, specially-designed spatula or syringes or the like, or by spray coating using innert gases, such as nitrogen, Freons or the like.

Surgical adhesive sheets may have any shape and size, for example, large ones of such as about 30 cm by about 30 cm in size, suitable for suture of skin and the like; small ones of such as about 2 mm by about 2 mm in size, suitable for anastomosis of arterioles, nerve and the like; and tape type ones of such as 2 mm–10 cm in width. They can be cut into a proper size for use.

Surgical adhesive sheets of the present invention can be applied in surgery, by various application methods as follows, which may be selected depending upon the part to be applied and application purpose.

(1) Transfer methods, by applying or sticking a adhesive sheet to the affected part, followed by transfering the adhesive to the part. For example, in case where a viscera is cut with a surgical knife, profuse bleeding occurs from the cutting surface. It is necessary to carry out hemostasis is needed to prevent bleeding, which can be attained with use of a surgical adhesive sheet of the invention. In this case, the adhesive sheet is sticked all over the affected part, and then the adhesive is transferred to the part along with carrying out pressure hemostasis to complete hemostasis. Sheet materials used in the adhesive sheets for this purpose are preferably films, non-adherent to surgical adhesive, for example, those made of silicone resin or fluorine-containing resin.

(2) Reinforcing methods, by applying or sticking a composite material comprising surgical adhesive combined with sheet to the part under force or the deficit part, for reinforcement and patching up. In the case used in living tissue, it is preferred to use biodegradable sheet.

(3) Wound protection methods, by applying or sticking a surgical adhesive sheet to the wounded part of such as wound of burn, for prevention of infect and acceleration of healing. For this purpose, preferred are sheet materials, permeable to water vapor or air, which include not only continuous films, but also films having a plurality of openings therein and non-woven fabrics. As another application, surgical adhesive sheet can be applied to skin closure and so on.

Surgical adhesives coated on sheets are cured with the presence of trace water (such as water contained in sheet material and moisture in air) to cause reduction adhesive power of surgical adhesive sheets. Therefore, it is necessary to use anhydrous ones as the sheet material and the other components, not to speak of the main components; and it is preferred to cut off air containing moisture during the preparation. Surgical adhesive sheets thus obtained can be stored for a long period of time within closed vessels capable of cutting off air and moisture.

A surgical instrument, in another aspect of the present invention, used for application of a surgical adhesive, comprises a non-adherent material towards an NCO-terminated urethane prepolymer. Suitable non-adherent materials include, for example, synthetic polymers, such as silicone resins, fluorine-containing resins, polyethylene resins, polypropylene resins and the like; as well as mixtures of two or more of these polymers and combinations of them with one or more of other polymers. Among these, preferred are silicone resins and fluorine-containing resins.

Figure 1:
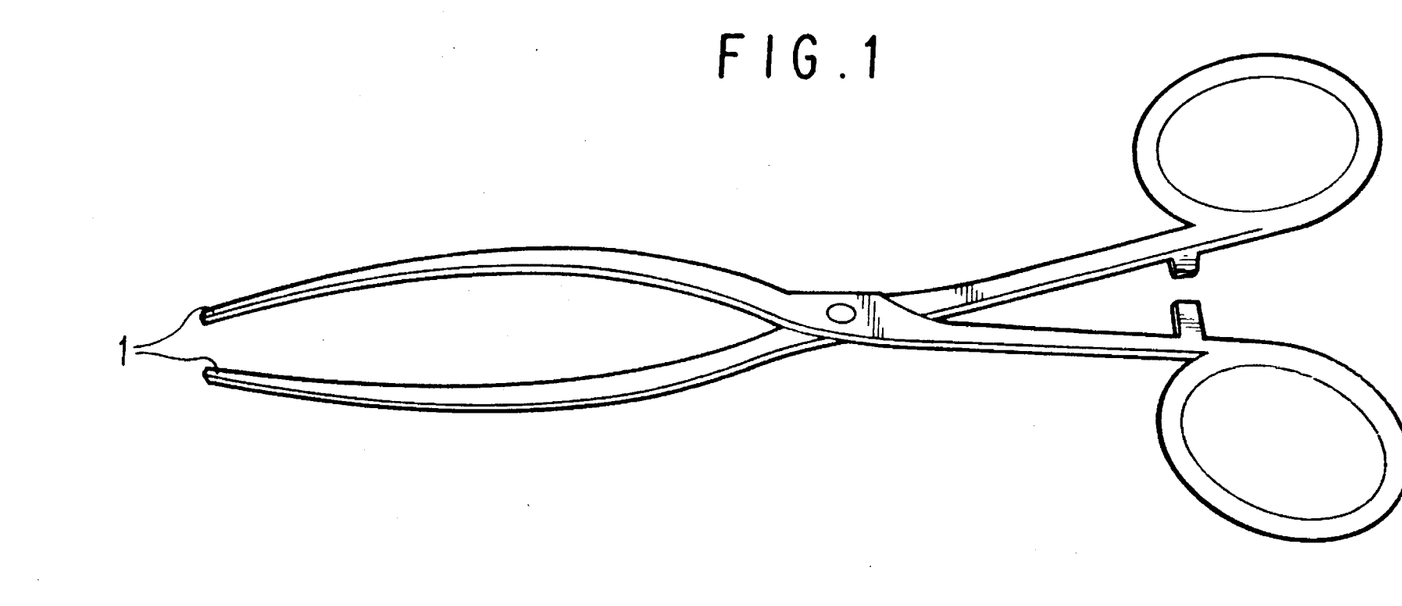
FIG. 1 is a perspective view of a forceps of the invention, coated with a fluorine resin.
Figure 2A:
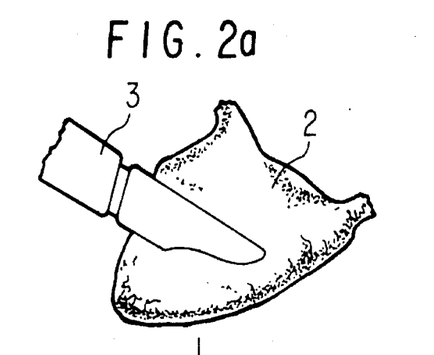
FIG. 2 is schematic representation of a process of hemostasis, using instruments of the invention which are a fluorine resin-coated forceps and a silocone plate.
Figure 2B:
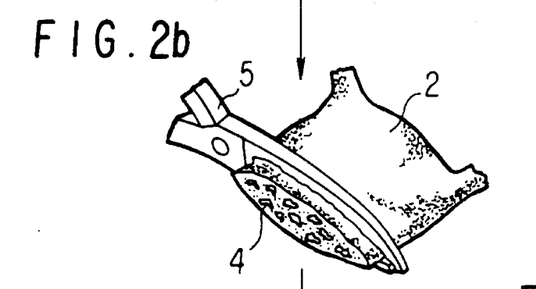
Figure 2C:
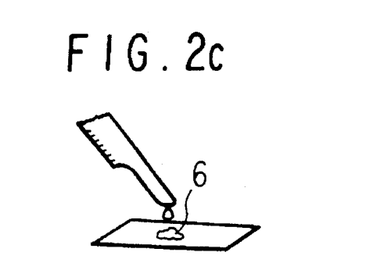
Figure 2D:
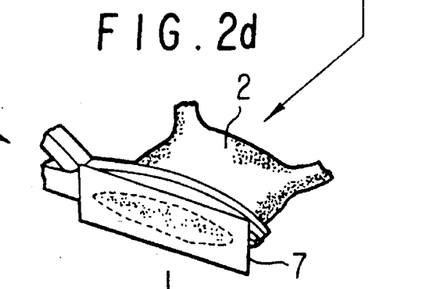
Figure 2E:
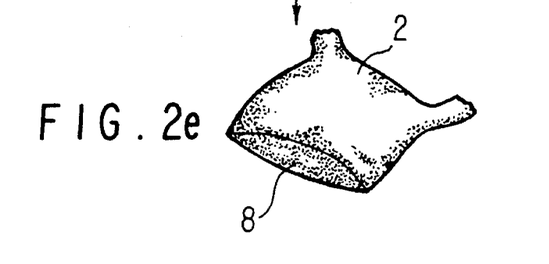

Surgical instruments of this invention are inclusive of conventional surgical instruments coated or lined with such a non-adherent material as above, and those made of such a non-adherent material itself. Such instruments include, for examples, spatulas, forceps (hemostatics forceps, typing forceps, alligator forceps, esophageal forceps and the like), pincets (tweezers), hookes, needle holders, separators, and the like. Illustrative of such instruments are forceps, as shown in FIG. 1, which are made of stainless steel, ends of which are coated with a resin (a fluorine containing resin) (1) non-adherent towards NCO-terminated urethane prepolymer.

Other examples of surgical instruments of the invention are ones newly designed suitable for application of the surgical adhesive to the affected part, for instance, those having shapes of film, plate or balloon.

Figure 4:
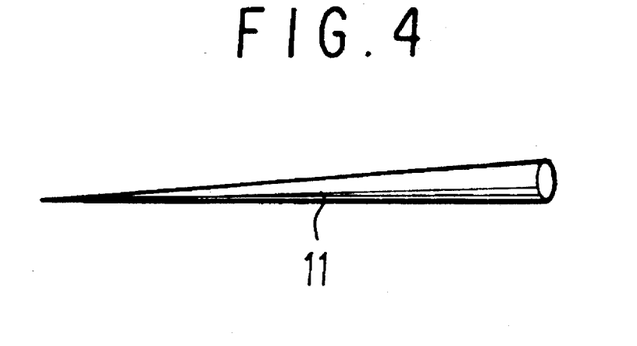
FIGS. 4 and FIG. 5 are perspective views of instruments for anastomosis of vessel of the invention.
Figure 5:
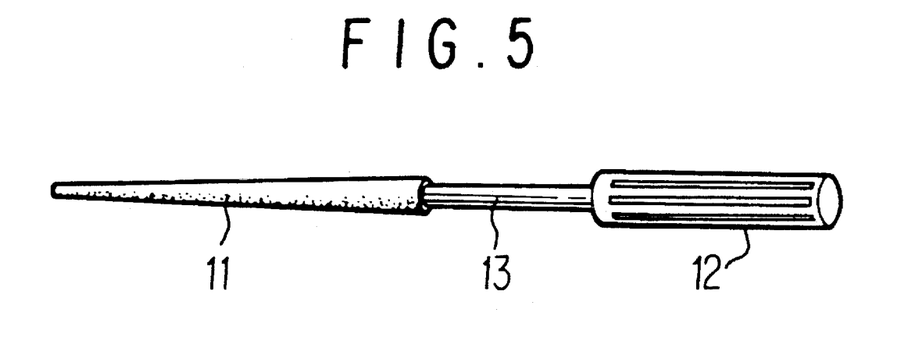

Instruments particularly suitable for anastomosis of blood vessel are those comprising a rod tapered so that the tip can be partly inserted into blood vessel. The tip of the rod may taper into a sharp point or conically, or the tip of the tapered rod may be cut or round off into a truncated cone or domed form. In case of rods made of soft materials, preferred are sharp-pointed ones, for easiness to deal with. Rods made of hard materials should be those of truncated cone or domed form, since sharp-pointed hard rods may be likely to injure vessel wall. It is required that the tip of the rod is tapered smaller than inner diameter of blood vessel to be applied, so as to be inserted thereinto, and the other end has an outer diameter larger than inner diameter of vessel. The tip inserted into vessel has an outer diameter of usually 3 mm or less, prefer ably 1 mm or less. The other end has an outer diameter of generally at least 3 mm, preferably 5–100 mm. The instruments include those comprising a tapered rod (11) alone, as shown in FIG. 4, and those comprising a tapered rod (11) and a handle (12), with or without a joint (13), as shown in FIG. 5.

Surgical instruments of the invention are suitable for use in application of surgical adhesive comprising NCO-terminated urethane prepolymer. Suitable surgical adhesives applicable with use of surgical instruments of the invention include the same ones as mentioned above, which comprises NCO-terminated urethane prepolymer and may contain one or more additives as above.

Surgical instruments of the invention can be used for application of the surgical adhesive to the affected part, as follows. In case of an instrument in the shape of film or plate, the surgical adhesive coated on the affected part is extended (or spreaded) under pressing with the instrument all over the part to be applied, whereby hemostasis of cut section of viscera can be attained effectively. An instrument in the form of balloon can be applied for pressing and extending of the surgical adhesive on uneven affected part. These instruments can attain not only application of surgical adhesive but also hemostasis under pressing at the same time, whereby remarkably improved curative effects of surgery can be obtained. Besides the method by extending the surgical adhesive on the affected part with the instrument, there may be mentioned a method comprising spreading the surgical adhesive on an instrument beforehand and transferring the adhesive onto the affected part. Application of surgical adhesive onto the affected part or the surgical instrument can be done by known means, for instance, by using brushes, tweezers, applicators, specially-designed spatula or syringes or the like, or by spray coating using innert gases, such as nitrogen, Freons or the like.

Surgical adhesive sheets and surgical instruments of this invention can be applied for bonding or hemostasis of tissues, such as blood vessels, heart, lung, esophagus, stomach, kidney, spleen, pancreas, duodenum, small intestine, large intestine, nerve, rectum, skin, and the like.

Treating methods using instruments of the invention are illustrated bellow in accordance with Figures.

FIG. 2 shows hemostasis treatment of a viscera after cutting, with use of an instrument of plate form. FIG. 2(a) shows cutting of a viscera (2) cut with a surgical knife (3). FIG. 2(b) shows section (4) of the viscera (2) clamped with application of fluorine resin-coated forceps (5) according to this invention. As shown in FIG. 2(c), a surgical adhesive (6) is coated on an instrument in the form of plate (7). As shown in FIG. 2(d), the plate (7) is pressed to the section of the viscera (2) to carry out hemostasis. FIG. 2(e) shows the stanched section (8) of the viscera (2), from which the plate (7) and the forceps (5) have being removed after curing of the surgical adhesive.

Figure 3A:
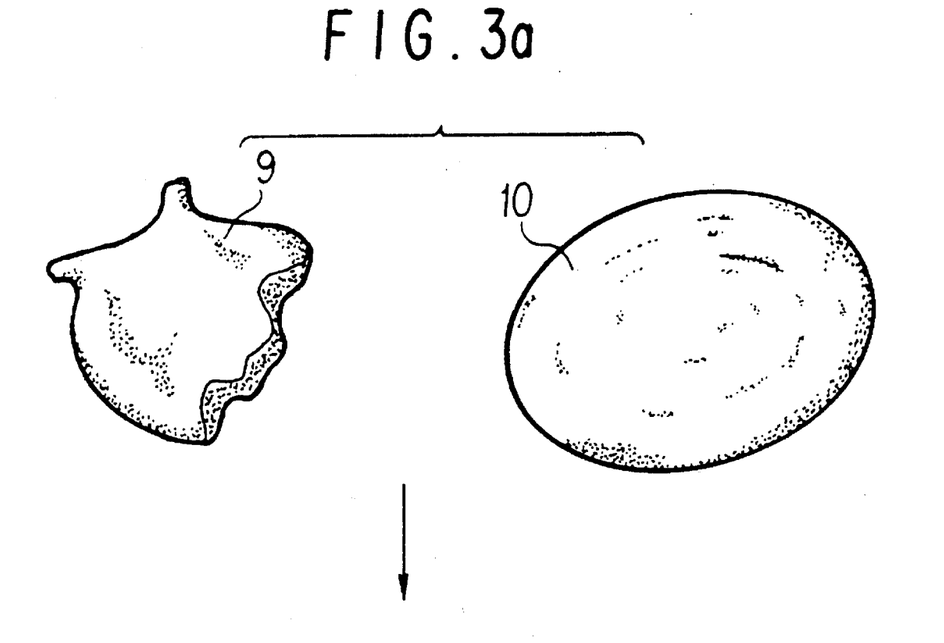
FIG. 3 is schematic representation of a process of hemostasis of a partly torn viscera, using a balloon instrument of the invention.
Figure 3B:
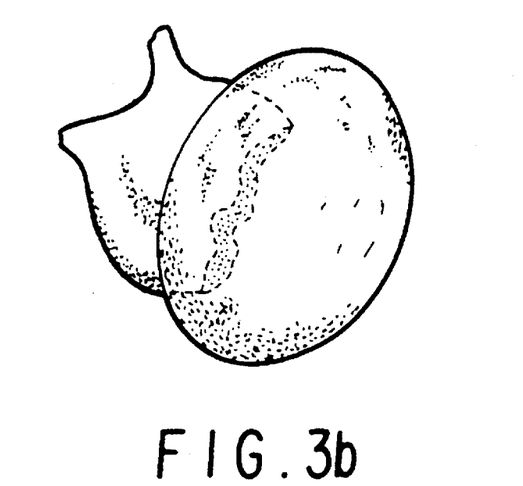

FIG. 3 shows hemostasis treatment of a partly torn viscera, with use of an instrument of balloon form. FIG. 3(a) shows a partly torn viscera (9) and an instrument in the form of balloon (10). A surgical adhesive is coated on the surface of the balloon (10), and the balloon (10) is pressed to the torn part of the viscera, as shown in FIG. 3(b) to perform hemostasis. As the balloon is capable of being deformed following to the torn part of the viscera, hemostasis is easily attained.

FIG. 6 shows anastomosis of blood vessels, with use of an instrument for anastomosis comprising a tapered rod of the invention.

Figure 6A:
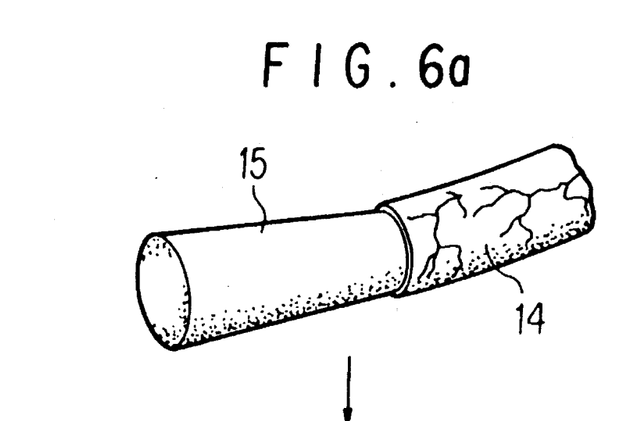
FIG. 6 is schematic representation of a process of anastomosis of vessel, using a tapered rod, an instrument of the invention.

1) Into a blood vessel (14), the tip of an instrument of tapered rod (15) is inserted, as shown in FIG. 6(a). (Only a part of the rod is inserted into the vessel, and the rest of the rod remained out of the vessel.)

Figure 6B:
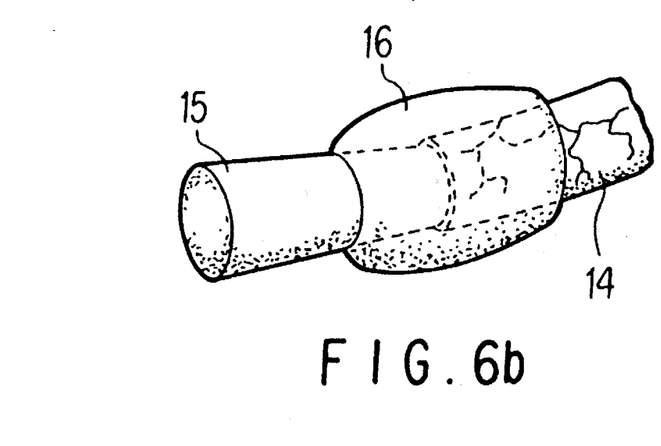

2) Then, surgical adhesive (16) is coated all around the vessel (14) and the rod (15) at the part where the rod is inserted into the vessel, as shown in FIG. 6(b).

3) After the adhesive has been cured into solid, the rod (15) is taken out of the vessel to obtain a vessel, the end of which has been fixed with the cured adhesive.

Figure 6C:
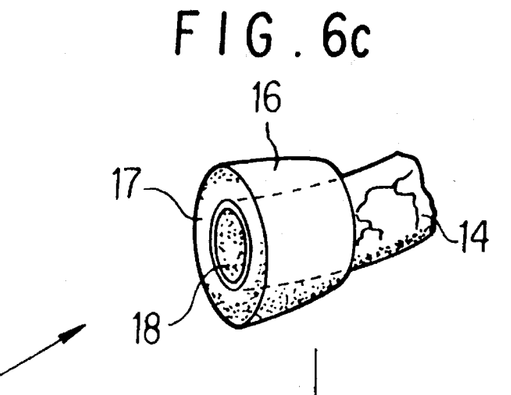

4) The cured adhesive (16) is cut together with the vessel, using a surgical knife or scissors to expose the section (18) of the vessel (14) fixed within the section (17) of the cured adhesive (16), as shown in FIG. 6(c).

5) Another blood vessel is treated in the same manner.

Figure 6D:
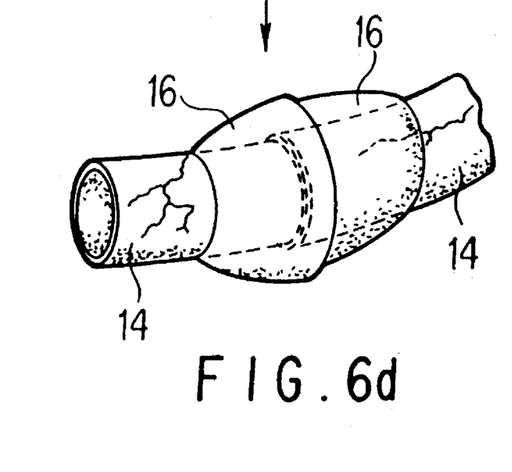

6) The two sections of vessels thus fixed are put together, as shown in FIG. 6(d), and then joined together by applying around them surgical adhesive and/or suture. (Surgical adhesive may be applied in the form of surgical adhesive sheet of this invention, or by using a surgical instrument of the invention.)

Having generally described the invention, a more complete understanding can be obtained by reference to certain specific examples, which are included for purposes of illustration only and are not intended to be limiting unless otherwise specified.

In the following, EO represents ethyleneoxide, PO represents propyleneoxide, and PTMG represents polytetramethyleneglycol. Urethane prepolymers were prepared by mixing under stirring polyisocyanate with polyether polyol dehydrated under reduced pressure and reacting them at a temperature of 80 degrees C. for 8 hours. Parts and % in Examples and Comparative Examples represent parts by weight and % by weight, respectively. Surgical adhesives used in Examples and Comparative Examples are as follows:

1) Adhesive A1: a surgical adhesive comprising an NCO-terminated hydrophilic urethane prepolymer having an NCO-content of 2.5%, obtained by reacting a polyether polyol [a EO/PO random copolymer having an average M.W. of 3,000 and oxyethylene content of 80%] with $OCN\text{-}CH_2(CF_2)_4CH_2\text{-}NCO$.

2) Adhesive A2: a surgical adhesive comprising an NCO-terminated hydrophilic urethane prepolymer having an NCO-content of 3.4%, obtained by reacting a polyether polyol [a EO/PO random copolymer having an average M.W. of 4,000 and oxyethylene content of 60%] with $OCN\text{-}CH_2(CF_2)_4CH_2\text{-}NCO$.

3) Adhesive A3: a surgical adhesive comprising an NCO-terminated hydrophilic urethane prepolymer having an NCO-content of 5.1%, obtained by reacting a polyether polyol [a PTMG/EO block copolymer having an average M.W. of 2,000 and oxyethylene content of 50%] with PPDI (p-phenylene diisocyanate.

4) Adhesive A4: a surgical adhesive comprising an NCO-terminated hydrophilic urethane prepolymer having an NCO-content of 3.4%, obtained by reacting a polyether polyol [a EO/PO random copolymer having an average M.W. of 4,000 and oxyethylene content of 60%] with PPDI.

EXAMPLE 1

A fluorine resin sheet (1.5 mm thick) was coated with Adhesive A1 (coating amount: 400 g/m$^2$) to obtain a surgical adhesive sheet.

Liver of a dog was clamped with forceps in accordance with an immaginal cutting line of about 2 cm length, and cut along with the inside of the forceps. The above surgical adhesive sheet was pressed to all over the section; and, after 5 minutes, the fluorine resin sheet was removed therefrom and the adhesive was transferred to the affected part. Whole the section was sealed completely and perfect hemostasis was attained, with very convenient handleability.

EXAMPLE 2

A non-woven fabric sheet (about 5 mm thick) comprising a copolymer of lactic acid and glycolic acid was coated with Adhesive A2 (coating amount: 300 g/m$^2$) to obtain a surgical adhesive sheet.

Spleen of a dog was clamped with forceps in accordance with an immaginal cutting line of about 2 cm length, and cut along with the inside of the forceps. Pressure hemostasis was carried out for 5 minutes with use of the above surgical adhesive sheet to all over the section, followed by removing the forceps therefrom. The section and the surgical adhesive sheet were integrated, and perfect hemostasis was attained, with very convenient handleability.

EXAMPLE 3

A polyurethane film (30 microns thick) was coated with a solution of 10 parts of Adhesive A1 diluted with 10 parts of ethyl acetate (coating amount: 400 g/m$^2$) to obtain a surgical adhesive sheet.

This surgical adhesive sheet was used for anastomosis for cut out parts of skin of rabbit back. The edges were placed closed to each other, and sticked together with the above adhesive sheet. After a week, the urethane film was peeled off. After 8 weeks, there was attained good cure of the affected part, without leaving substantial scare of the cut out parts. Very convenient handleability as also obtained.

EXAMPLE 4

A non-woven fabric sheet (30 microns thick) composed of a polyglycolic acid was coated with Adhesive A1 in an amount of 100 g/m$^2$ followed by coating the surface with silver sulfadiazine as an bactericide to obtain a surgical adhesive sheet.

Mouse loss of skin (1 cm×1 cm) was formed surgically; and, after inoculation with *Pseudomonas aeruginosa*, the above surgical adhesive sheet was sticked thereto. After 8 weeks, there was attained good cure of the affected part, without impediment by infection.

EXAMPLE 5

Forceps and pincers made of stainless steel were surface-coated with a fluorine resin to prepare surgical instruments of the present invention. A plate made of a fluorine resin was prepared to obtain an surgical instrument of this invention.

Spleen of a dog was clamped with the above forceps of this invention in accordance with an immaginal cutting line of about 2 cm length, and cut along with the inside of the forceps. The above fluorine resin plate of the invention was coated with Adhesive A1, and pressed to all over the section. After 5 minutes, the plate was removed therefrom and the adhesive was transferred to the affected part. Whole the section was sealed completely and perfect hemostasis was attained. Though the adhesive had been adhered to the forceps, the pincers and the plate, they were removed with no particular resistance, without injuring the affected part, and no bleeding was occurred any more. By using the instruments of this invention, surgical adhesive can be deeled with very conveniently, in spite of its high viscosity.

EXAMPLE 6

Forceps and pincers made of stainless steel were surface-coated with a fluorine resin to prepare surgical instruments of the present invention. A balloon made of a silicone resin was prepared to obtain an surgical instrument of this invention.

Liver of a dog was clamped with the above forceps of the invention in accordance with an immaginal cutting line of about 4 cm length; and cut off, making brakes, along with the inside of the forceps. The above silicone resin balloon of the invention was coated with Adhesive A4, and pressed to all over the section of the liver. After 5 minutes, the balloon was removed therefrom and the adhesive was transferred to the affected part. Whole the section was sealed completely and perfect hemostasis was attained. Though the adhesive had been adhered to the forceps, the pincers and the balloon, they were removed with no particular resistance, without injuring the affected part, and no bleeding was occurred any more. By using the instruments of this invention, surgical adhesive can be deeled with very conveniently, in spite of its high viscosity.

EXAMPLE 7

A rod of a fluorine resin (copolymer of tetrafluoroethylene and perfluoroalkyl vinyl ether) was tapered into a cone (diameter of the base: 5 mm; length: 150 mm) to obtain an instrument for anastomosis of blood vessel according to the present invention.

Arteriole (outer diameter : about 1.5 mm) of a dog was clamped with forceps, and was temporally ligated and cut in two, followed by end-to-end anastomosis.

Into one blood vessel, was inserted the sharp-tip of the above instrument, the larger end thereof being remained out of the vessel, whereby the vessel was plugged. Adhesive A1 was coated around the end (inserted part) of the vessel. After 8 minutes, the adhesive was cured, and then the instrument was removed out of the vessel, followed by cutting off the cured adhesive together with the vessel with use of surgical knife. There was obtained an annular adhesive end, wherein the vessel section was kept circular within the adhesive section.

The other blood vessel was treated similarly.

The two sections of vessels thus obtained were put together, handling with the adhesive parts, and then surgical adhesive was applied again around them to perform anastomosis. After 5 minutes, current of blood was reopened, but no bleeding was observed, and smooth flow of blood and good recovery were obtained.

EXAMPLE 8

A conical needle of stainless steel, the tip of which had been cut off (diameter of the base: 7 mm, diameter of the tip: 0.5 mm and length: 150 mm), was coated with a silicone resin to obtain an instrument for anastomosis of blood vessel according to the present invention.

Artery (outer diameter : about 3 mm) of a dog was clamped with forceps, and was temporally ligated, followed by end-to-side anastomosis using vein. From the fact that a vein as transplantable blood vessel have biscuspid valve and blood flows only one direction, the direction of transplantation was confirmed.

Into one end of transplantable blood vessel, was inserted the tip of the above instrument, the larger end thereof being remained out of the vessel, whereby the vessel was plugged. Adhesive A1 was coated around the end (inserted part) of the vessel. After the adhesive was cured, the instrument was removed out of the vessel, followed by cutting off the cured adhesive together with the vessel with use of surgical knife. There was obtained an annular adhesive end, wherein the vessel section was kept circular within the adhesive section.

Then, an anastomosis part of a host blood vessel was treated similarly; and, after curing of the adhesive, a side wall of the vessel was cut off so as to provide a elliptical open cut part.

The two sections of vessels thus obtained are put together, handling with the adhesive parts, and then two stitches of stay suture was applied thereto, followed by applying surgical adhesive again around them to perform anastomosis. After 5 minutes, current of blood was reopened, but no bleeding was observed, and smooth flow of blood and good recovery were obtained.

Comparative Example 1

Forceps, spatula and pincers used in the following Comparative Examples were conventional ones made of stainless steel.

Liver of a dog was clamped with forceps in accordance with an immaginal cutting line of about 2 cm length, and cut along with the inside of the forceps. Adhesive A1 was coated onto all over the section with a spatula; and, after 5 minutes, the forceps was removed therefrom. In coating of Adhesive A1, the prepolymer was also adhered to other visceras such as stomach, because of high viscosity. And, in removing the forceps, the adhesive having sealed all over the section was pulled with adhesion to the forceps, and the surrounding seal was partly peeled off to cause bleeding again.

Comparative Example 2

Liver of a dog was clamped with conventional forceps in accordance with an immaginal cutting line of about 4 cm length; and cut off, making brakes, along with the inside of the forceps to obtain a model of partly torn liver. Adhesive A4 was coated onto all over the section with a spatula to carry out hemostasis. In coating of surgical adhesive, it is difficult to coat prepolumer up to the insides of the brakes, and large amount of the adhesive was adhered to other visceras, because of high viscosity. And, in removing the forceps, the adhesive having sealed all over the section was pulled with adhesion to the forceps, and the surrounding seal was partly peeled off to cause bleeding again.

Comparative Example 3

Arteriole (outer diameter: about 1.5 mm) of a dog was clamped with forceps, and was temporally ligated and cut in two, followed by end-to-end anastomosis.

The two sections of vessels were put together, and then two stitches of stay suture was applied thereto, followed by applying surgical adhesive A1 around them to perform anastomosis. After 5 minutes, current of blood was reopened; and good adhesion was obtained, but blood flow was not smooth and obliteration was occurred after operation, as vessel sections at joint were not maintained sufficiently.

Surgical adhesive sheets of the present invention make it possible to apply only a necessary amount to a fixed place to be bound, by cutting the sheet into a desired size; and, as compared with surgical adhesives of the prior art, a remarkable improvement in handleability can be attained by this invention. There can be exhibited, in the place of medical treatment, considerable effects in reliability and reduction of operation time, without necessity of any special instruments and techniques. In addition, surgical adhesive sheets of the invention, in which surgical adhesive is used not alone but combined with sheet into composite, make it possible applying to operations in the form not as mere bonding material but as reinforcing materials, such as patch treatment for parts broken off.

Surgical instruments according to the present invention can attain, keeping merits of surgical adhesive comprising NCO-terminated urethane prepolymer, effects as follows:

1) Surgical adhesives, which have high viscosity and have heretofore been of poor handleability and difficult to be applied to a fixed place to be bound in only a necessary amount, can be easily treated and applied to a fixed place to be bound in only a necessary amount, by using the instruments of this invention, particularly those having shapes of film, plate and balloon.

2) Surgical instruments of the invention, coated or lined with material non-adherent to urethane prepolymer, can be easily removed from the adhesive and the affected parts without resistance, even when the adhesive is adhered to the instruments and the affected parts, so the instruments can be used without fear of reblooding by force to the affected parts.

Application of adhesive sheets of the invention to surgical operation, or application of surgical adhesive with use of surgical instruments of the invention makes it possible to perform operation with method of adhesion, instead of suturing in conventional operation. There can be attained remarkable improvements in medical technology, such as hemostasis, prevention of leaking enzyme from viscera or the like, prevention of minute blood vessel occusion, and nerve anastomosis, as well as provisional fixing before suturing, and ensuring of bonding by combination of adhesion with suturing. Furthermore, the invention can provide high reliance and high efficiency, not only in operation, but also in medical treatment at large, for example, joining of incised wound or culting portions, adhesive treatment in dental surgery, curative means by controlled release of drugs in combination with physiologically active materials, and so on.

Instruments comprising a tapered rod in accordance with the invention are useful as instruments for anastomosis of blood vessel, which make the best use of adhesion properties of surgical adhesive. That is:

1) By inserting the tip of the instrument into blood vessel, the inner section of the vessel can be maintained sufficiently.

2) Use of surgical adhesive with the instrument can provide cut section of shape easily deeled with.

3) As the instrument has a tapered form, the instrument of a size can be applied for most vessels of various thickness (diameter).

4) Using of the instrument for anastomosis of blood vessel makes it possible to carry out anastomosis of capillary vessel safely and within a short period of time and to avoid obliteration of vessel during anastomosis, which had been considered difficult hitherto.

5) In addition, the instruments of the invention are useful not only for anastomosis of arterioles, but also for bonding of general tubular living tissues (for example, blood vessels in general, including veins; lymphatic vessels, trachea, bronchial tubes, digestive tubular organs and the like), and can provide high reliability and high performance over the whole field of medical treatments.

What is claimed as new and desired to be secured by Letters Patent is:

1. A method of surgical bonding or hemostasis of tissue, comprising applying a surgical adhesive sheet comprising a substantially anhydrous biodegradable sheet material coated with a surgical adhesive comprising an NCO-terminated urethane prepolymer directly to said tissue, said substantially anhydrous sheet material being selected from the group consisting of polyamino acids, polyamino acid copolymers, oxidized cellulose, chitin, collagen, polylactic acids, polyglycolic acids, polyhydroxybutyric acids, and copolymers of lactic acid and glycolic acid.

2. A method of surgical bonding or hemostasis of tissue, comprising applying a surgical adhesive sheet comprising applying a surgical adhesive sheet comprising a substantially anhydrous sheet material coated with a fluorine-containing polyisocyanate directly to said tissue, and removing said sheet material.

3. A method of surgical bonding or hemostasis of tissue, comprising applying a surgical adhesive sheet comprising a substantially anhydrous non-biodegradable sheet material coated with a surgical adhesive comprising an NCO-terminated urethane prepolymer directly to said tissue, and removing said sheet material, said non-biodegradable sheet material comprising at least one polymer selected from the group consisting of polyurethane resins, silicone resins and fluorine-containing resins.

* * * * *

UNITED STATES PATENT AND TRADEMARK OFFICE
CERTIFICATE OF CORRECTION

PATENT NO.   : 5,457,141
DATED        : October 10, 1995
INVENTOR(S)  : Takehisa MATSUDA, et al.

It is certified that error appears in the above-indentified patent and that said Letters Patent is hereby corrected as shown below:

Please delete the second and third Foreign Application Priority Dates and Numbers from Item [30] on the title page.

Signed and Sealed this

Thirtieth Day of January, 1996

Attest:

BRUCE LEHMAN

Attesting Officer          Commissioner of Patents and Trademarks